United States Patent [19]

Dolman et al.

[11] Patent Number: 4,649,154
[45] Date of Patent: Mar. 10, 1987

[54] FUNGICIDAL AND/OR BACTERICIDAL COMPOSITIONS CONTAINING NITROTHIOPHENES, AND USE THEREOF

[75] Inventors: Hendrik Dolman; Johannes Kuipers, both of Weesp, Netherlands

[73] Assignee: Duphar International Research B.V., Weesp, Netherlands

[21] Appl. No.: 543,895

[22] Filed: Oct. 20, 1983

Related U.S. Application Data

[60] Division of Ser. No. 361,758, Mar. 25, 1982, Pat. No. 4,451,660, which is a continuation-in-part of Ser. No. 217,172, Dec. 16, 1980, abandoned.

[30] Foreign Application Priority Data

Dec. 19, 1979 [NL] Netherlands ............... 7909124

[51] Int. Cl.$^4$ ........................................... A01N 43/02
[52] U.S. Cl. ..................................... 514/445; 514/336
[58] Field of Search ............................. 514/445, 336

[56] References Cited

U.S. PATENT DOCUMENTS 2,389,128 11/1945 Bambas .................. 549/63
4,451,660 5/1984 Dolman et al. ........... 549/63

OTHER PUBLICATIONS

Chem. Abst., vol. 74, (1971), 22634q.

Primary Examiner—Alan Siegel
Attorney, Agent, or Firm—Stevens, Davis, Miller & Mosher

[57] ABSTRACT

The invention relates to new nitrothiophenes of the general formula

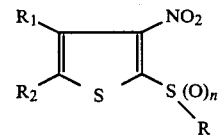

wherein
R is an alkyl group having 1 to 12 carbon atoms, which alkyl group may be substituted with a phenyl group substituted, if desired, with nitro, halogen, alkyl with 1 to 4 carbon atoms or alkoxy with 1 to 4 carbon atoms, with an alkoxycarbonyl group having 2 to 5 carbon atoms, or with a thiocyanato group,
or R is a phenyl group, a pyridyl group or an N-oxypyridyl group, which groups may be substituted with nitro, halogen, alkyl with 1 to 4 carbon atoms, or alkoxy with 1 to 4 carbon atoms;
$R_1$ is a hydrogen atom, a halogen atom, an alkyl group having 1 to 4 carbon atoms, or a phenyl group substituted or not substituted with nitro, halogen, alkyl with 1 to 4 carbon atoms, or alkoxy with 1 to 4 carbon atoms;
$R_2$ is a hydrogen atom, an alkyl group having 1 to 4 carbon atoms, a cyano group, an alkanoyl group having 1 to 5 carbon atoms, an $\alpha,\alpha$-dialkoxyalkyl- or $\alpha,\alpha$-alkylenedioxyalkyl group having 3 to 10 carbon atoms, a carboxy group, an alkoxycarbonyl group having 2 to 5 carbon atoms, an $\alpha$-hydroxyalkyl group having 1 to 4 carbon atoms, an $\alpha$-haloalkyl group having 1 to 4 carbon atoms, an $\alpha$-alkoxyalkyl group having 2 to 6 carbon atoms, an alkoxycarboximidoyl group having 2 to 5 carbon atoms, a sulpho group, an amino-, alkylamino- or dialkylaminosulphonyl group, the alkyl group(s) of which has (have) 1 to 4 carbon atoms, or an alkoxysulphonyl group having 1 to 4 carbon atoms, and
n is 0 to 2.

The compositions are particularly suitable to prevent infections by phytophagous microorganisms in agriculture and horticulture. For this purpose, the seed is treated prior to sowing or the soil destined for sowing or planting is treated with the composition in a dosage from 100 to 1,500 mg of active substance per kg of seed and from 2 to 100 kg of active substance per hectare, respectively.

11 Claims, No Drawings

FUNGICIDAL AND/OR BACTERICIDAL COMPOSITIONS CONTAINING NITROTHIOPHENES, AND USE THEREOF

REFERENCE TO RELATED APPLICATONS

This is a division of application Ser. No. 361,758 filed Mar. 25, 1982, now U.S. Pat. No. 4,451,660, which in turn is a continuation-in-part of application Ser. No. 217,172 filed Dec. 16, 1980 and now abandoned.

BACKGROUND OF THE INVENTION

The invention relates to new nitrothiophenes and fungicidal and/or bactericidal compositions, particularly compositions for the treatment of soil or seed against phytophagous microorganisms, which compositions contain the new nitrothiophenes as active substances, and to the use of these compositions in agriculture and horticulture.

DISCUSSION OF THE PRIOR ART

German Offenlegungsschrift No. 2,627,328 discloses nitrothiazoles with fungicidal activity, for example, for the treatment of seeds. A compound described in this application is 2-methylsulphinyl-4-methyl-5-nitrothiazole.

GENERAL DESCRIPTION OF THE INVENTION

The present invention relates to new compounds of the general formula

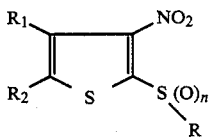

wherein

R is an alkyl group having 1 to 12 carbon atoms, which alkyl group may be substituted with a phenyl group substituted, if desired, with nitro, halogen, alkyl with 1 to 4 carbon atoms or alkoxy with 1 to 4 carbon atoms, with an alkoxycarbonyl group having 2 to 5 carbon atoms, or with a thiocyanato group, or R is a phenyl group, a pyridyl group or an N-oxypyridyl group, which groups may be substituted with nitro, halogen, alkyl with 1 to 4 carbon atoms, or alkoxy with 1 to 4 carbon atoms;

$R_1$ is a hydrogen atom, a halogen atom, an alkyl group having 1 to 4 carbon atoms, or a phenyl group optionally substituted with nitro, halogen, alkyl with 1 to 4 carbon atoms, or alkoxy with 1 to 4 carbon atoms;

$R_2$ is a hydrogen atom, an alkyl group having 1 to 4 carbon atoms, a cyano group, an alkanoyl group having 1 to 5 carbon atoms, an α,α-dialkoxyalkyl- or α,α-alkylenedioxyalkyl group having 3 to 10 carbon atoms, a carboxy group, an alkoxycarbonyl group having 2 to 5 carbon atoms, an α-hydroxyalkyl group having 1 to 4 carbon atoms, an α-haloalkyl group having 1 to 4 carbon atoms an α-alkoxyalkyl group having 2 to 6 carbon atoms, an alkoxycarboximidoyl group having 2 to 5 carbon atoms, sulpho group, an amino-, alkylamino- or dialkylaminosulphonyl group, the alkyl group(s) of which has (have) 1 to 4 carbon atoms, or an alkoxysulphonyl group having 1 to 4 carbon atoms, and n is 0 to 2.

Of these new compounds, those which have been shown to have excellent suitability as fungicides and/or bactericides, are compounds of the general formula

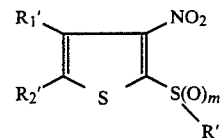

wherein

R' is an alkyl group with 1 to 4 carbon atoms, m is 0 or 1, and, if m is 0, $R_1'$ and $R_2'$ are both hydrogen atoms, and, if m is 1, $R_1'$ is a hydrogen atom or an alkyl group with 1 to 4 carbon atoms and $R_2'$ is a hydrogen atom or an acetyl group.

Examples of new nitrothiophenes according to the present invention that have a high fungicidal and/or bactericidal activity are:

(1) 2-methylsulphinyl-3-nitrothiophene,
(2) 2-methylsulphinyl-3-nitro-4-methylthiophene,
(3) 2-ethylsulphinyl-3-nitrothiophene,
(4) 2-n-propylsulphinyl-3-nitrothiophene,
(5) 2-isobutylsulphinyl-3-nitrothiophene,
(6) 2-ethylthio-3-nitrothiophene, and
(7) 2-methylsulphinyl-3-nitro-5-acetylthiophene.

Examples of other new nitrothiophenes according to the present invention that have a fungicidal and/or bactericidal activity are:

(8) 2-methylsulphinyl-3-nitro-5-ethoxycarbonylthiophene,
(9) 2-methylsulphinyl-3-nitro-5-ethoxycarboximidoylthiophene,
(10) 2-methylsulphinyl-3-nitro-5-cyanothiophene,
(11) 2-methylsulphonyl-3-nitrothiophene,
(12) 2-methylsulphonyl-3-nitro-4-methylthiophene,
(13) 2-methylsulphinyl-3-nitro-4,5-dimethylthiophene,
(14) 2-phenylsulphinyl-3-nitrothiophene,
(15) 2-[3-nitrothienyl(-2)sulphinyl]pyridine-N-oxide,
(16) 2-(4-methoxyphenylsulphinyl)-3-nitrothiophene,
(17) 2-(4-chlorophenylsulphinyl)-3-nitrothiophene,
(18) 2-(4-nitrophenylsulphinyl)-3-nitrothiophene,
(19) 2-methylsulphinyl-3-nitro-4-phenylthiophene,
(20) 2-methylsulphonyl-3-nitro-4-phenylthiophene,
(21) 2-ethylsulphonyl-3-nitrothiophene,
(22) 2-n-propylsulphonyl-3-nitrothiophene,
(23) 2-n-heptylsulphinyl-3-nitrothiophene,
(24) 2-methylsulphonyl-3-nitro-5-cyanothiophene,
(25) 2-ethoxycarbonylmethylsulphonyl-3-nitrothiophene,
(26) 2-ethoxycarbonylmethylsulphinyl-3-nitrothiophene,
(27) 2-[3-nitro-5-cyanothienyl(-2)sulphinyl]pyridine-N-oxide,
(28) 2-phenylsulphinyl-3-nitro-5-cyanothiophene,
(29) 2-phenylsulphonyl-3-nitro-5-cyanothiophene,
(30) 2-[3-nitrothienyl(-2)sulphinyl]-3-nitropyridine,
(31) 2-methylsulphonyl-3-nitro-5-acetylthiophene,
(32) 2-methylsulphinyl-3-nitro-4-chlorothiophene,
(33) 2-thiocyanatomethylsulphonyl-3-nitrothiophene,
(34) 2-thiocyanatomethylsulphinyl-3-nitrothiophene,
(35) 2-thiocyanatomethylthio-3-nitrothiophene,
(36) 2-[3-nitro-5-formylthienyl(-2)thio]pyridine-N-oxide,

(37) 2-methylthio-3-nitro-4-methylthiophene,
(38) 2-methylsulphinyl-3-nitro-5-N,N-dimethylaminosulphonylthiophene,
(39) 2-methylsulphonyl-3-nitro-5-N,N-dimethylaminosulphonylthiophene,
(40) 2-ethylsulphinyl-3-nitro-5acetylthiophene
(41) 2-ethylsulphonyl-3-nitro-5-acetylthiophene,
(42) 2-methylsulphinyl-3-nitro-5-hydroxymethylthiophene,
(43) 2-methylsulphonyl-3-nitro-5-hydroxymethylthiophene,
(44) 2-methylsulphinyl-3-nitro-5-(1-hydroxyethyl)thiophene,
(45) 2-methylsulphonyl-3-nitro-5-(1-hydroxyethyl)thiophene,
(46) 2-methylsulphinyl-3-nitro-5-ethylenedioxymethylthiophene,
(47) 2-methylsulphonyl-3-nitro-5-ethylenedioxymethylthiophene, and
(48) 2-methylsulphinyl-3-nitro-5-bromomethylthiophene.

The new compounds according to the present invention show a strong fungicidal activity with respect to a wide spectrum of pathogenic fungi which may occur in agricultural and horticultural crops, for example, *Phytophthora infestans* on tomato, *Sphaerotheca fuliginea* on cucumber, *Uromyces phaseoli* on bean, and *Pyricularia oryzae* on rice.

It has been found that the new compounds according to the present invention are particularly active against phytophagous microorganisms, e.g., against phytophagous soil fungi ("soil-borne diseases"), for example, Pythium spp. (for example, *Pythium ultimum*) and *Rhizoctonia solani*, against phytophagous fungi which are transferred with the seed ("seed-borne diseases"), for example *Pyrenophora graminea* on barley, *Tilletia caries* on wheat, Fusarium spp. (for example, *Fusarium nivale*) on wheat and Ustilago spp. (for example, *Ustilago avenae*) on oats, and against phytophagous bacteria, for example, *Erwinia carotovora*.

The new compounds according to the present invention are considerably more effective than 2-methylsulphinyl-4-methyl-5-nitrothiazole disclosed in the above-mentioned German Offenlegungsschrift, as will become apparent from the examples. Infections with phytophagous bacteria and/or fungi, e.g., phytophagous soil fungi or fungi which are transferred with the seed, can be prevented by treating the soil destined for planting or sowing, or, which will usually be preferred for economical reasons, the seed itself with a composition which comprises a new compound according to the invention.

For practical applications, the substances in accordance with the present invention are processed to compositions. In such compositions, the active substance is mixed with solid carrier material or dissolved or dispersed in liquid carrier material, and if desired, in combination with auxiliary substances, for example, emulsifiers, wetting agents, dispersion agents, and stabilizers.

Examples of compositions according to the present invention are aqueous solutions and dispersions, oily solutions and oily dispersions, solutions in organic solvents, pastes, dusting powders, dispersing powders, miscible oils, granules, pellets, invert emulsions, aerosol compositions, and fumigating candles.

Dispersible powders, pastes, and miscible oils are compositions in concentrate form which are diluted prior to or during use.

The invert emulsions and solutions in organic solvents are mainly used for application by air, namely when large areas are treated with a comparatively small quantity of composition. The invert emulsion can be prepared shortly before or even during spraying in the spraying apparatus by emulsifying water in an oily solution or an oily dispersion of the active substance. The solutions of the active substance in organic solvents may be provided with a phytotoxicity-reducing substance, for example, wool fat, wool fatty acid, or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired, in the presence of a binder, on granular carrier material, for example, porous granules (e.g., pumice and attaclay), mineral non-porous granules (sand or ground marlow), organic granules (e.g., dried coffee grounds, cut tobacco stems, and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and agglomerating the mixture then to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example, kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example, the lignin sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils, the active compound is dissolved in a suitable solvent which preferably is poorly water-miscible, and one or more emulsifiers are added to this solution. Suitable solvents are, for example, xylene, toluene, petroleum distillates which are rich in aromatics, for example, solvent naphtha, distilled tar oil, and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol or glycol ether, to which solution a dispersion agent and, if desired, a surface-active substance, has been added. When diluting with water shortly before or during spraying, an aqueous dispersion of the active substance is then obtained.

An aerosol composition according to the present invention is obtained in the usual manner by incorporating the active substance, if desired, in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen, and nitrous oxide.

Fumigating candles or fumigating powders, i.e., compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and, furthermore, a substance to delay combustion, for example, kaolin, bentonite and/or colloidal silicic acid.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives," for example, polyvinylalcohol cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the present invention. As a result of this, the activity spectrum of the composition is widened and synergism may occur.

For use in such a combination composition are to be considered the following known insecticidal, acaricidal and fungicidal compounds.

Insecticides, for example 1. organic chlorine compounds, for example, 6,7,8,9,10,10-hexachloro-1,5,5a,6,9,9a-hexahydro-6,9-methano-2,4,3-benzo[e]dioxathiepine-3-oxide;
2. carbamates, for example, 2-dimethylamino-5,6-dimethylpyrimidin-4-yl dimethyl carbamate and 2-isopropoxyphenylmethylcarbamate;
3. di(m)ethylphosphates, for example, 2-chloro-2-diethylcarbamoyl-1-methylvinyl—, 2-methoxycarbonyl-1-methylvinyl—, 2-chloro-1-(2,4-dichlorophenyl)-vinyl—, and 2-chloro-1-(2,4,5-trichlorophenyl)vinyl di(m)ethyl phosphate;
4. 0,0-di(m)ethyl phosphorothioates, for example, O(S)-2-methylthioethyl—, S-2-ethylsulphinylethyl—, S-2-(1-methylcarbamoylethylthio)ethyl—, 0-4-bromo-2,5-dichlorophenyl—, 0-3,5,6-trichloro-2-pyridyl—, 0-2-isopropyl-6-methylpyrimidin-4-yl—, and 0-4-nitrophenyl 0,0-di(m)ethyl phosphorothioate;
5. 0,0-di(m)ethyl phosphorodithioates, for example, S-methylcarbamoylmethyl—, S-2-ethylthioethyl—, S-(3,4-dihydro-4-oxobenzo [d]-1,2,3-triazin-3-ylmethyl—, S-1,2-di(ethoxycarbonyl)ethyl—, S-6-chloro-2-oxobenzoxazolin-3-ylmethyl—, and S-2,3-dihydro-5-methoxy-2-oxo-1,3,4-thiadiazol-3-yl-methyl 0,0-di(m) ethyl phosphorodithioate;
6. phosphonates, for example, dimethyl 2,2,2-trichloro-1-hydroxyethylphosphonate;
7. benzoylurea, for example, N-(2,6-difluorobenzoyl)-N'-(4-chlorophenyl)urea;
8. natural and synthetic pyrethroids;
9. amidines, for example, N'-(2-methyl-4-chlorophenyl)-N,N-dimethylformamidine; and
10. microbial insecticides, such as Bacillus thuringiensis.

Acaricides, for example 1. organic tin compounds, for example, tricyclohexyl tin hydroxide and di[tri-(2-methyl-2-phenylpropyl)tin-]oxide;
2. organic halogen compounds, for example, isopropyl 4,4'-dibromobenzilate, 2,2,2-trichloro-1,1-di(4-chlorophenyl)ethanol and 2,4,5,4'-tetrachlorodiphenyl sulphone; and, furthermore: 3-chloro-α-ethoxyimino-2,6-dimethoxybenzyl benzoate and 0,0-dimethyl S-methylcarbamoyl methyl phosphorothioate.

Fungicides, for example 1. organic tin compounds, for example, triphenyl tin hydroxide an triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole (-2) carbamates and 1,2-bis (3-alkoxycarbonyl-2-thiureido)benzene, and furthermore, 2,4-dinitro-6-(2-octylphenyl-crotonate), 1-[bis(dimethylamino) phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidinemethanol, 1-(isopropylcarbamoyl)-3-(3,5-dichlorophenyl) hydantoin, N-(1,1,2,2-tetrachloroethylthio)-4-cyclohexene-1, 2-carboximide, N-trichloromethylmercapto-4-cyclohexene-1,2-dicarboximide, N-tridecyl-2,6-dimethylmorpholine, and 5,6-dihydro-2-methyl-1,4-oxathiine-3-carboxanilide.

The dosages of the composition according to the invention desired for practical application will, of course, depend on various factors, for example, field of application, selected active substance, form of composition, nature and extent of the infection, and the weather conditions. In general, favorable results are achieved with a dosage which corresponds to 250 to 1000 g of the active substance per hectare. When applied against phytophagous microorganisms good results are achieved when the soil is treated with a composition comprising an amount of active compound which corresponds to 2 to 100 kg of active substance per ha. When applied to the seed itself a dosage is preferred which corresponds to 100 to 1500 mg of active substance per kg of seed.

The compounds according to the invention are new compounds which can be prepared in a manner known per se for the synthesis of related compounds. For example, the new compounds of the general formula

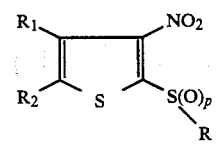

wherein

R, $R_1$ and $R_2$ have the above meanings, and
p is 1 or 2,
can be prepared by reacting a compound of the general formula

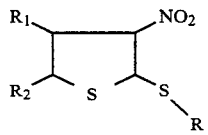

with an oxidizing agent. Suitable oxidizing agents are hydrogen peroxide and peroxycarboxylic acids, for example, peracetic acid, or a substituted perbenzoic acid such as p-nitroperbenzoic acid or m-chloroperbenzoic acid. For the preparation of the sulphone, hydrogen peroxide is preferably used as an oxidizing agent. When peroxycarboxylic acids, for example, p-nitroperbenzoic acid or m-chloroperbenzoic acid, are used, the sulphide is oxidized selectively to the sulphoxide. These oxidation reactions are preferably carried out in a polar organic solvent, for example, acetic acid, an alcohol such as methanol, or a chlorinated hydrocarbon, for example, chloroform. The reaction temperature depends on the reagents used and the selected solvent, and may vary between 0° C. and the boiling point of the solvent. After isolating the final product, it may be purified, if desired, by recrystallization.

The above thiocompounds of the general formula

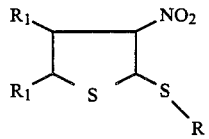

can be prepared by converting the corresponding 2-halogen compound with a suitable alkali mercaptide. The reaction is carried out in an inert polar organic solvent, e.g., an alcohol such as ethanol, at a reaction temperature between 0° C. and the boiling point of the solvent.

2-(substituted)alkylthio-3-nitrothiophenes can also be prepared according to a method described by Henriksen and Autrup in Acta Chem. Scand. 24 (1970), 2629–2633. According to this method, a 2-nitroethylene-1,1-dithiolate is reacted with an α-halogen aldehyde or ketone, succeeded by ring closure and reaction with a suitable (substituted) alkylhalogenide.

When in the above formula $R_2$ is an alkoxycarboximidoyl group, this thiocompound can be prepared by reacting the corresponding 2-halo-3-nitro-5-cyanothiophene with an alkalimercaptide in the presence of a suitable alcohol.

Thiocompounds of the above general formula, in which $R_2$ is a cyano group, can be prepared in a manner known per se for the synthesis of related compounds, for example, by reacting the corresponding 2-thio-3-nitro-5-formyl-thiophene, preferably in sodium formiate-formic acid, with hydroxyl amine; the 2-thio-3-nitro-5-formyl-thiophene compound can be prepared by converting the corresponding halogen compound with a suitable alkalimercaptide.

The invention will now be described in greater detail with reference to the following specific examples.

EXAMPLE I

Preparation of 2-methylsulphinyl-3-nitrothiophene

There was added 0.95 g of p-nitroperbenzoic acid to a solution of 0.88 g of 2-methylthio-3-nitrothiophene in 15 ml of chloroform at a temperature from 0° to 10° C. After stirring for 2 hours at 5° C., a solution of 2 g of sodium bicarbonate in approximately 50 ml of water was added; the reaction mixture was then stirred for 15 minutes. The chloroform layer was separated, washed with water, and filtered. After distilling the solvent, the desired product was obtained in a yield of 0.95 g; melting-point 155° C.

The following compounds were prepared in a corresponding manner in which, if desired, m-chloroperbenzoic acid was used as an oxidizing agent and methanol as a solvent.

2-methylsulphinyl-3-nitro-4-methylthiophene, m.p. 142° C.;
2-methylsulphinyl-3-nitro-5-ethoxycarboximidoyl thiophene, m.p. 10° C.;
2-methylsulphinyl-3-nitro-5-cyanothiophene, m.p. 160° C.;
2-methylsulphinyl-3-nitro-4,5-dimethylthiophene, m.p. 156° C.;
2-(4-chlorophenylsulphinyl)-3-nitrothiophene, m.p. 163°–165° C.;
2-phenylsulphinyl-3-nitrothiophene, m.p. 124°–126° C.;
2-(4-methoxyphenylsulphinyl)-3-nitrothiophene, m.p. 156°–157° C.;
2-methylsulphinyl-3-nitro-5-ethoxycarbonylthiophene, m.p. 95°–99° C.;
2-ethylsulphinyl-3-nitrothiophene, m.p. 79°–82° C.;
2-n-propylsulphinyl-3-nitrothiophene, m.p. 81°–84° C.;
2-isobutylsulphinyl-3-nitrothiophene, m.p. 91°–93° C.;
2-methylsulphinyl-3-nitro-5-acetylthiophene, m.p. 161°–163° C.;
2-[3-nitrothienyl(-2)sulphinyl]pyridine-N-oxide, m.p. 174° C. (decomp.);
2-(4-nitrophenylsulphinyl)-3-nitrothiophene, m.p. 194°–196° C.;
2-methylsulphinyl-3-nitro-4-phenylthiophene, m.p. 171°–173° C.;
2-n-heptylsulphinyl-3-nitrothiophene, m.p. 68°–71° C.;
2-ethoxycarbonylmethylsulphinyl-3-nitrothiophene, m.p. 52°–54° C.;
2-[3-nitro-5-cyanothienyl(-2)sulphinyl]pyridine-N-oxide, m.p. 158° C. (decomp.);
2-phenylsulphinyl-3-nitro-5-cyanothiophene, m.p. 158°–160° C.;
2-[3-nitrothienyl(-2)sulphinyl]-3-nitropyridine, m.p. 181°–183° C. decomp.);
2-methylsulphinyl-3-nitro-4-chlorothiophene, m.p. 114°–116° C.;
2-thiocyanatomethylsulphinyl-3-nitrothiophene, m.p. 138°–140° C.;
2-methylsulphinyl-3-nitro-5-N,N-dimethylaminosulphonylthiophene, m.p 153°–154° C.;
2-ethylsulphinyl-3-nitro-5-acetylthiophene, m.p. 146° C. (decomp.);
2-methylsulphinyl-3-nitro-5-hydroxymethylthiophene, m.p. 112.5°–113.5° C.;
2-methylsulphinyl-3-nitro-5-(1-hydroxyethyl)thiophene, m.p. 118.5°–120.5° C.;
2-methylsulphinyl-3-nitro-5-ethylenedioxymethylthiophene, m.p. 125°–126.5° C.; and 2-methylsulphinyl-3-nitro-5-bromomethylthiophene, m.p. 138°–139° C.

EXAMPLE II

Preparation of 2-methylsulphonyl-3-nitrothiophene

There was added 1.25 ml of a 33% solution of hydrogen peroxide in water to a solution of 0.88 g of 2-methylthio-3-nitrothiophene in 10 ml of acetic acid at approximately 100° C. After heating at approximately 100° C. for approximately 30 minutes, another 1.25 ml of the same hydrogen peroxide solution were added. After heating at approximately 100° C. for 3 hours, the reaction mixture was cooled and poured in water. The precipitate of 2-methylsulphonyl-3-nitrothiophene was sucked off and dried; weight 0.85 g; melting-point 121° C.

In a corresponding manner, the following compounds were prepared:
2-methylsulphonyl-3-nitro-4-methylthiophene, m.p. 130° C.;
2-methylsulphonyl-3-nitro-4-phenylthiophene, m.p. 119°–120° C.;
2-ethylsulphonyl-3-nitrothiophene, m.p. 84°–86° C.;
2-n-propylsulphonyl-3-nitrothiophene, m.p. 49°–52° C.;
2-methylsulphonyl-3-nitro-5-cyanothiophene, m.p. 175°–177° C.;
2-ethoxycarbonylmethylsulphonyl-3-nitrothiophene, m.p. 96°–98° C.;
2-phenylsulphonyl-3-nitro-5-cyanothiophene, m.p. 178°–180° C.;
2-methylsulphonyl-3-nitro-5-acetylthiophene, m.p. 160°–161° C.;
2-thiocyanatomethylsulphonyl-3-nitrothiophene, m.p. 144°–147° C.;
2-methylsulphonyl-3-nitro-5-N,N-dimethylaminosulphonylthiophene, m.p 175°–176° C.;
2-ethylsulphonyl-3-nitro-5-acetylthiophene, m.p. 137.5°–138.5° C.;
2-methylsulphonyl-3-nitro-5-hydroxymethylthiophene, m.p. 101.5°–102.5° C.;
2-methylsulphonyl-3-nitro-5-(1-hydroxyethyl)thiophene, m.p. 91°–92° C.; and
2-methylsulphonyl-3-nitro-5-ethylenedioxymethylthiophene, m.p. 142°–143° C.

EXAMPLE III

Preparation of 2-methylthio-3-nitro-5-acetylthiophene

Liquid methylmercaptan (4 ml) was added to a solution of 0.82 g of Na in 50 ml of absolute ethanol. The resulting solution was added to a solution of 7.2 g of 2-chloro-3-nitro-5-acetylthiophene in 200 ml of absolute ethanol in 15 minutes at 5° C. After stirring at room temperature for 30 minutes, 100 ml of water was added, after which the precipitate was sucked off and washed successively with water and isopropanol. The precipitate was boiled a moment with 300 ml of carbontetrachloride, cooled down, and sucked off. After drying the title compound was obtained in a yield of 6.4 g; m.p. 191°–193° C.

In a corresponding manner the following compound was prepared.
2-[3-nitro-5-formylthienyl(-2)thio]pyridine-N-oxide, m.p. 165° C. (decomp.).

EXAMPLE IV

Preparation of 2-thiocyanomethylthio-3-nitrothiophene

A solution of 12.8 ml of monochloroacetaldehyde in 12.8 ml of water was added to a solution of 35.0 g dipotassium 2-nitroethylene 1,1-dithiolate in 225 ml of water, while stirring at room temperature. The reaction mixture was cooled down to 0° C., after which successively 16 ml of concentrated hydrochloric acid and 16 ml of concentrated potassium hydroxide were added, both for 5 minutes; after each addition the reaction mixture was stirred for 5 minutes. Thereafter 13 ml of chloromethylthiocyanate was added in 5 minutes. The reaction mixture was stirred at room temperature during 1.5 hour, and was left to stand overnight. Dichloromethane was added and the reaction mixture was stirred at room temperature during 0.5 hour. After sucking off solid material, the dichloromethane layer was separated and washed with water. The solvent was evaporated and the product was obtained by purification via column chromatography. The desired product was obtained in a yield of 7.1 g; m.p. 86°–87° C.

In a corresponding manner the following compounds were prepared:
2-ethylthio-3-nitrothiophene, m.p. 51°–53° C.; and
2-methylthio-3-nitro-4-methylthiothiophene, m.p. 104° C.

EXAMPLE V

Preparation of 2-methylthio-3-nitro-5-cyanothiophene

A sodium methyl mercaptide solution was prepared by adding 5 ml of methylmercaptan to 1.75 g of Na in 60 ml of absolute ethanol. While stirring and cooling this solution to below 10° C. it was added to a solution of 17.6 g of 2-bromo-3-nitro-5-formylthiophene in 200 ml of ethanol. After stirring at room temperature for another 2 hours, 200 ml of water were added, after which the formed precipitate was sucked off, washed with water-ethanol mixture (1:1 v/v), and recrystallized from isopropanol. 6.5 g of 2-methylthio-3-nitro-5-formylthiophene of melting point 129°–131° C. were obtained. Then 2.35 g of $NaHCO_3$, 3.1 g of 2-methylthio-3-nitro-5-formylthiophene, and 1.2 g of $NH_2OH.HCl$ were added successively to 50 ml of formic acid. The reaction mixture was refluxed for 1 hour, after which, water was added and the formed precipitate was sucked off. After recrystallization from isopropanol the desired 2-methylthio-3-nitro-5-cyanthiophene was obtained in a yield of 2.3 g; melting point 150° C.

EXAMPLE VI

Test on activity against Pythium spp. and Rhizoctonia solani; soil treatment.

Compositions of the compounds to be tested were prepared by suspending 15 mg of the active substances in 20 ml of water; 1 kg of soil infected with Pythium spp. and *Rhizoctonia solani* was mixed with this composition. Because Pythium spp. and *Rhizoctoni solani* develop excellently in the soil on corn grains and flax stalks, respectively, corn grains and flax stalks were added to the soil ("trapping"). After 4 days at 20° C. in the glass-house, the corn grains and the flax stalks were rinsed with tap water an laid on an artificial culture medium which consisted of 2% Bacto agar in water. After an incubation period of 24 hours at 23° C. it was tested whether, and if so to what extent, the fungi had developed. Table A shows this development. When the development has been flourishing, this is denoted by "—". A partial development is denoted by "±". When the fungi on the culture medium have not developed, the active substance has had a good activity; this is denoted by "+" in the Table. The compound numbers refer to the corresponding compounds listed previously in the specification.

TABLE A

| Compound no. | Dosage in mg/kg of soil | Development of the fungi |
|---|---|---|
| (1) | 15 | + |
| (2) | 15 | + |
| (9) | 15 | + |
| (10) | 15 | + |
| (11) | 15 | + |
| (13) | 15 | ± |
| 2-methylsulphinyl-4-methyl-5-nitrothiazole (known) | 15 | — |
| control | — | — |

EXAMPLE VII

Test with respect to the protection of seedlings against a plant pathogenic soil fungus, namely, Pythium spp., by means of a seed treatment The compounds to be tested were processed to compositions by pulverizing them and then mixing them in the desired concentration (see Table B) with kaolin.

Beet seed was treated with these compositions in a quantity of 6 g of composition per kg of seed and then sowed in trays containing soil which was badly infected with Pythium spp. After 3 weeks in a glass-house at 18°-22° C. and a relative humidity of 70-100%, the percentage of come-up and healthy seedlings was determined. The results are recorded in Table B.

TABLE B

| Compound no. | Dosage in mg of active substance per kg of seed | Percentage come-up and healthy plants |
|---|---|---|
| (1) | 1500 | 100 |
| | 600 | 95 |
| (2) | 1500 | 80 |
| | 600 | 62 |
| (13) | 1500 | 95 |
| | 600 | 40 |
| (10) | 1500 | 98 |
| | 600 | 75 |
| (9) | 1500 | 97 |
| | 600 | 70 |
| (17) | 1500 | 45 |
| | 600 | 30 |
| (16) | 1500 | 50 |
| | 600 | 35 |
| (14) | 1500 | 75 |
| | 600 | 30 |
| (15) | 1500 | 80 |
| | 600 | 42 |
| (11) | 1500 | 98 |
| | 600 | 75 |
| (12) | 1500 | 80 |
| | 600 | 65 |
| (40) | 1500 | 100 |
| | 600 | 95 |
| (43) | 1500 | 100 |
| | 600 | 95 |
| control (kaolin) | — | 5 |

EXAMPLE VIII

Test with respect to the protection of seedling against a plant pathogenic seed fungus, namely, Fusarium nivale, by means of a seed treatment Wheat seed, infected with Fusarium nivale, was treated with 3 g of a composition obtained according to Example VII per kg of seed and was then sowed in trays containing soil. These trays were placed in a Wisconsin tank having a soil temperature of 8°-12° C. After 3 weeks the number of come-up and healthy plants was determined. The come-up of plants from untreated seed served for control and has arbitrarily been fixed at 100. The results are recorded in Table C.

TABLE C

| Compound no. | Dosage in mg of active substance per kg of seed | Percentage of come-up and healthy plants |
|---|---|---|
| (1) | 750 | 148 |
| | 600 | 143 |
| | 300 | 137 |
| (11) | 750 | 145 |
| | 300 | 130 |
| (2) | 600 | 128 |
| | 300 | 124 |
| (13) | 600 | 134 |
| | 300 | 120 |
| (9) | 600 | 135 |
| | 300 | 113 |
| (8) | 600 | 134 |
| | 300 | 106 |
| control | — | 100 |

EXAMPLE IX

Field experiments with respect to the protection of seedlings against various plant pathogenic seed fungi by means of a seed treatment Wheat seed, infected with Tilletia caries, barley seed, infected with Pyrenophora graminea and Ustilago nuda, respectively and oats seed, infected with Ustilago avenae, were treated with 3 g of a composition obtained according to Example VII per kg of seeds. The seeds were then sowed in the field in tracks of two running meters. Each experiment was carried out in quintuplicate. After the spike formation, the number of sick plants was determined with reference to spike symtoms. The results recorded in Table D were obtained.

TABLE D

| Compound no. | Dosage in mg of active substance per kg of seeds | Percentage of diseased plants | | |
|---|---|---|---|---|
| | | Wheat/ T. ca. | Barley/ P. gra. | Oats/ U. av. |
| (1) | 1200 | 0.0 | 0.0 | 1.9 |
| | 600 | 1.2 | 2.4 | 5.1 |
| | 300 | 2.2 | 8.2 | 9.4 |
| (2) | 1200 | 0.0 | | 7.0 |
| | 600 | 0.2 | | 7.5 |
| (13) | 1200 | 0.2 | | 7.8 |
| | 600 | 1.4 | | 7.5 |
| control | — | 24.4 | 24.2 | 27.2 |

In the same way a second series of field experiments was carried out. The results are presented in Table E. In the last three columns the percentage of diseased plants is shown in comparison with that from untreated seed. The percentage of diseased plants from untreated seed has arbitrarily been fixed at 10.

TABLE E

| Compound no. | Dosage in mg of active substance per kg of seeds | Percentage of diseased plants | | |
|---|---|---|---|---|
| | | Wheat/ T. ca. | Barley/ P. gra. | Oats/ U. av. |
| (1) | 300 | 44 | 14 | 9 |
| | 600 | 18 | 3 | 8 |
| | 900 | 24 | 8 | 5 |
| (2) | 300 | 20 | 23 | 52 |
| | 600 | 18 | 12 | 13 |
| | 900 | 10 | 16 | 15 |
| (13) | 300 | 60 | 13 | 31 |
| | 600 | 51 | 17 | 28 |
| | 900 | 13 | 5 | 16 |
| (3) | 300 | 55 | 15 | 19 |
| | 600 | 15 | 6 | 5 |
| | 900 | 18 | 6 | 7 |
| (6) | 300 | 81 | 5 | 89 |
| | 600 | 65 | 2 | 73 |
| | 900 | 69 | 2 | 41 |
| (4) | 300 | 97 | 20 | 88 |
| | 600 | 53 | 14 | 51 |
| | 900 | 45 | 3 | 36 |
| (5) | 300 | 91 | 15 | 60 |
| | 600 | 78 | 3 | 29 |
| | 900 | 35 | 2 | 21 |
| control | — | 100 | 100 | 100 |

EXAMPLE X

Test on activity against leaf fungi

The compounds to be tested were processed to compositions by dispersing the compounds in water by means of a dispersing agent, for example, lignin sulphonate, and/or a wetting agent, for example, naphthalene sulphonate, an alkylbenzene sulphonate, an alkyl polyoxyethylene or an alkylaryl polyoxyethylene. The crop to be protected against false mildew on tomato (*Phytophthora infestans*) was treated with these compositons by spraying young tomato plants, approximately 10 cm high, with the above suspensions of the active substances in the concentration indicated in Table F below. The plants thus treated were then infected with *Phytophthora infestans* by spraying the plants with an aqueous suspension containing per ml 100,000 spores of *Phytophthora infestans*. After an incubation period of 4 days at a temperature of 18° C. and a relative humidity of 100%, it was determined to what extent the fungi had developed During the incubation period, a light-dark cycle of 16/8 hours had been used.

The results of the treatment are recorded in Table F. In this Table, the concentration of the compound used is indicated in mg of active substance per liter and the protection against *Phytophthora infestans* which was found with this concentration: 100% means total protection, 0% means no protection.

In the same manner as described above, young dwarf French beans, approximately 10 cm high, were treated against rust of beans (*Uromyces phaseoli*). Infecting the plants was done with an aqueous suspension containing 300,000 spores of *Uromyces phaseoli* per ml. The incubation period was 10 days at a temperature of 18° C. and a relative humidity of 100%. The results obtained are also recorded in Table F.

TABLE F

| Compound no. | Concentration in mg of active substance per liter | % Protection | |
|---|---|---|---|
| | | bean/ U. pha. | tomato/ P. inf. |
| (1) | 300 | 100 | 100 |
| (2) | 300 | 100 | 70 |
| (13) | 300 | 100 | 55 |
| (11) | 300 | 100 | 100 |
| (12) | 300 | 100 | 70 |
| 2-methylsulphinyl-4-methyl-5-nitro-thiazole (known) | 300 | 0 | 0 |
| control | — | 0 | 0 |

EXAMPLE XI

In vitro test on activity against phytophagous microorganisms.

The compounds to be tested were incorporated into a culture medium, consisting of 1% by weight of glucose, 0.2% by weight of a yeast extract (marmite), 0.5% by weight of a protein (pepton), 2.5% by weight of agar-agar and 95.8% by weight of distilled water, in Petri dishes in concentrations of 10, 30, and 100 ppm. The Petri dishes were inoculated with the plantpathogenic fungi *Fusarium nivale*, *Rhizoctonia solani* and *Pythium ultimum* and the plantpathogenic bacterium *Erwinia carotovora*, and then kept at a temperature of 20° C. After 48 hours, the growth inhibiting activity of the compounds was determined visually; the results are recorded in Table G.

TABLE G

| Compound no. | Concentration in ppm | % inhibition of the growth of the fungus/bacterium | | | |
|---|---|---|---|---|---|
| | | Fusarium niv. | Rhizoct. sol. | Pyth. ult. | Erw. car. |
| (1) | 10 | 65 | 30 | 100 | 100 |
| | 30 | 100 | 50 | 100 | 100 |
| | 100 | 100 | 100 | 100 | 100 |
| (2) | 10 | 65 | 15 | 100 | 50 |
| | 30 | 100 | 60 | 100 | 100 |
| | 100 | 100 | 85 | 100 | 100 |
| (13) | 10 | 0 | 20 | 60 | 0 |
| | 30 | 45 | 55 | 100 | 0 |
| | 100 | 100 | 65 | 100 | 100 |
| (10) | 10 | 20 | 40 | 45 | 100 |
| | 30 | 55 | 55 | 75 | 100 |
| | 100 | 100 | 60 | 100 | 100 |
| (9) | 10 | 0 | 5 | 25 | 0 |
| | 30 | 50 | 50 | 25 | 100 |
| | 100 | 85 | 65 | 90 | 100 |
| (8) | 10 | 10 | 15 | 25 | 0 |
| | 30 | 85 | 55 | 80 | 100 |
| | 100 | 100 | 75 | 100 | 100 |
| (19) | 10 | 65 | 10 | 100 | 0 |
| | 30 | 100 | 50 | 100 | 0 |
| | 100 | 100 | 65 | 100 | 50 |
| (7) | 10 | 65 | 30 | 75 | 50 |
| | 30 | 100 | 40 | 100 | 100 |
| | 100 | 100 | 100 | 100 | 100 |
| (32) | 10 | 10 | 40 | 65 | 100 |
| | 30 | 35 | 65 | 100 | 100 |
| | 100 | 100 | 65 | 100 | 100 |
| (15) | 10 | 70 | 5 | 55 | 50 |
| | 30 | 100 | 35 | 90 | 100 |
| | 100 | 100 | 70 | 100 | 100 |
| (27) | 10 | 15 | 15 | 0 | 100 |
| | 30 | 100 | 35 | 80 | 100 |
| | 100 | 100 | 50 | 100 | 100 |
| (28) | 10 | 0 | 20 | 40 | 0 |
| | 30 | 25 | 55 | 60 | 50 |
| | 100 | 65 | 60 | 100 | 100 |
| (3) | 10 | 65 | 30 | 100 | 50 |
| | 30 | 100 | 70 | 100 | 100 |
| | 100 | 100 | 100 | 100 | 100 |
| (4) | 10 | 65 | 15 | 80 | 50 |
| | 30 | 100 | 70 | 100 | 50 |
| | 100 | 100 | 85 | 100 | 100 |

TABLE G-continued

| Compound no. | Concentration in ppm | \% inhibition of the growth of the fungus/bacterium | | | |
|---|---|---|---|---|---|
| | | Fusarium niv. | Rhizoct. sol. | Pyth. ult. | Erw. car. |
| (5) | 10 | 70 | 25 | 80 | 0 |
| | 30 | 100 | 60 | 100 | 0 |
| | 100 | 100 | 85 | 100 | 50 |
| (23) | 10 | 60 | 60 | 80 | 0 |
| | 30 | 70 | 80 | 100 | 0 |
| | 100 | 70 | 85 | 100 | 0 |
| (26) | 10 | 45 | 20 | 40 | 0 |
| | 30 | 50 | 50 | 85 | 50 |
| | 100 | 100 | 65 | 100 | 100 |
| (18) | 10 | 55 | 50 | 45 | 50 |
| | 30 | 100 | 65 | 100 | 100 |
| | 100 | 70x | 35x | 30x | 50x |
| (34) | 10 | 25 | 15 | 35 | 50 |
| | 30 | 50 | 40 | 85 | 100 |
| | 100 | 100 | 60 | 100 | 100 |
| (30) | 10 | 20 | 15 | 45 | 100 |
| | 30 | 55 | 30 | 75 | 100 |
| | 100 | 100 | 70 | 100 | 100 |
| (11) | 10 | 35 | 30 | 35 | 50 |
| | 30 | 80 | 50 | 90 | 100 |
| | 100 | 100 | 65 | 100 | 100 |
| (12) | 10 | 0 | 35 | 50 | 0 |
| | 30 | 35 | 45 | 100 | 0 |
| | 100 | 35 | 70 | 100 | 0 |
| (31) | 10 | 0 | 30 | 50 | 100 |
| | 30 | 80 | 65 | 65 | 100 |
| | 100 | 45x | 65x | 100x | 100x |
| (33) | 10 | 0 | 0 | 15 | 100 |
| | 30 | 35 | 10 | 40 | 100 |
| | 100 | 45 | 60 | 75 | 100 |
| (20) | 10 | 35 | 45 | 20 | 0 |
| | 30 | 55 | 55 | 30 | 50 |
| | 100 | 45x | 50x | 30x | 50x |
| (21) | 10 | 35 | 15 | 20 | 0 |
| | 30 | 35 | 25 | 70 | 50 |
| | 100 | 100 | 50 | 100 | 100 |
| (22) | 10 | 35 | 15 | 0 | 0 |
| | 30 | 95 | 50 | 50 | 50 |
| | 100 | 100 | 60 | 100 | 100 |
| (24) | 10 | 25 | 35 | 0 | 50 |
| | 30 | 50 | 55 | 55 | 100 |
| | 100 | 90 | 60 | 100 | 100 |
| (25) | 10 | 20 | 25 | 0 | 50 |
| | 30 | 65 | 25 | 30 | 50 |
| | 100 | 90 | 40 | 100 | 100 |
| (29) | 10 | 25 | 40 | 15 | 50 |
| | 30 | 35x | 40x | 25x | 100x |
| | 100 | 50x | 55x | 40x | 100x |
| (37) | 10 | 15 | 50 | 0 | 0 |
| | 30 | 55 | 85 | 65 | 0 |
| | 100 | 55x | 55x | 75x | 0x |
| (6) | 10 | 85 | 20 | 75 | 100 |
| | 30 | 100 | 65 | 100 | 100 |
| | 100 | 100 | 100 | 100 | 100 |
| (35) | 10 | 0 | 35 | 75 | 0 |
| | 30 | 100 | 35 | 100 | 100 |
| | 100 | 100 | 35 | 100 | 100 |
| (36) | 10 | 0 | 45 | 0 | 0 |
| | 30 | 45 | 80 | 50 | 0 |
| | 100 | 100 | 85 | 100 | 0 |
| (38) | 10 | 15 | | 31 | |
| | 30 | 47 | | 31 | |
| | 100 | 52 | | 100 | |
| (39) | 10 | 28 | | 56 | |
| | 30 | 42 | | 56 | |
| | 100 | 61 | | 80 | |
| (40) | 10 | 64 | | 42 | |
| | 30 | 71 | | 82 | |
| | 100 | 100 | | 100 | |
| (41) | 10 | 59 | | 43 | |
| | 30 | 64 | | 46 | |
| | 100 | 100 | | 91 | |
| (42) | 10 | 30 | | 70 | |
| | 30 | 20 | | 67 | |
| | 100 | 100 | | 100 | |
| (43) | 10 | 23 | | 52 | |
| | 30 | 25 | | 46 | |
| | 100 | 64 | | 77 | |
| (44) | 10 | 30 | | 70 | |
| | 30 | 30 | | 85 | |
| | 100 | 100 | | 100 | |
| (45) | 10 | 8 | | 45 | |
| | 30 | 8 | | 45 | |
| | 100 | 57 | | 91 | |
| (46) | 10 | 71 | | 45 | |
| | 30 | 66 | | 74 | |
| | 100 | 100 | | 100 | |
| (47) | 10 | 25 | | 50 | |
| | 30 | 49 | | 60 | |
| | 100 | 100 | | 100 | |
| (48) | 10 | 76 | | 62 | |
| | 30 | 78 | | 84 | |
| | 100 | 100 | | 100 | |
| control | — | 0 | 0 | 0 | 0 | x Note: crystallization of active compound.

What we claim is:

1. A fungicidal and/or bactericidal composition, comprising (a) a fungicidally and/or bactericidally effective amount of a compound of the formula

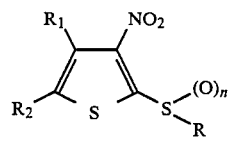

wherein
R is selected from the group consisting of
$C_1$–$C_{12}$ alkyl,
Phneyl-substituted $C_1$–$C_{12}$ alkyl
substituted phenyl-substituted $C_1$–$C_{12}$ alkyl wherein the phenyl substituent is selected from the group consisting of nitro, a halogen atom, $C_1$–$C_4$ alkyl, and $C_1$–$C_4$ alkoxy,
$C_2$–$C_5$ alkoxy carbonyl-substituted $C_1$–$C_{12}$ alkyl,
thiocyanato-substituted $C_1$–$C_{12}$ alkyl,
phneyl,
phenyl substituted with a member selected from the group consisting of nitro, a halogen atom, $C_1$–$C_4$ alkyl, and $C_1$–$C_4$ alkoxy,
pyridyl,
pyridyl substituted with a member selected from the group consisting of nitro, a halogen atom, $C_1$–$C_4$ alkyl, and $C_1$–$C_4$ alkoxy,
N-oxypyridyl, and
N-oxypyridyl substituted with a member selected from the group consisting of nitro, a halogen atom, $C_1$–$C_4$ alkyl, and $C_1$–$C_4$ alkoxy;
$R_1$ is selected from the group consisting of
a hydrogen atom,
a halogen atom,
$C_1$–$C_4$ alkyl,
phenyl, and
phenyl substituted with a member selected from the group consisting of nitro, a halogen atom, $C_1$–$C_4$ alkyl, and $C_1$–$C_4$ alkoxy;
$R_2$ is selected from the group consisting of
a hydrogen atom,
$C_1$–$C_4$ alkyl,
cyano, $C_1$–$C_5$ alkanoyl,
$C_3$–$C_{10}$ α, α-dialkoxyalkyl,
$C_3$–$C_{10}$ α, α-alkylenedioxyalkyl,
carboxy,
$C_2$–$C_5$ alkoxycarbonyl,
$C_1$–$C_4$ α-hydroxyalkyl,
$C_1$–$C_4$ α-haloalkyl,
$C_2$–$C_6$ α-alkoxyalkyl,
$C_2$–$C_5$ alkoxycarboximidoyl
sulpho,
aminosulphonyl,
$C_1$–$C_4$ alkylaminosulphonyl,
$C_2$–$C_8$ dialkylaminosulphonyl, and
$C_1$–$C_4$ alkoxysulphonyl; and
n is 1 or 2,
with the proviso that when $R_1$ and $R_2$ are hydrogen atoms, n is 1, and (b) a liquid or solid inert carrier.

2. A composition for the treatment of soil or seed against phytophagous microorganisms, comprising a phytophagous microorganism reducing effective amount of a composition as defined in claim 1.

3. A composition as defined in claim 1 or claim 2, wherein the active constituent is a compound of the formula

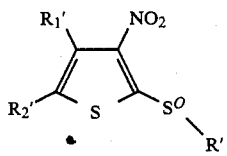

wherein

R' is $C_1$–$C_4$ alkyl,
$R_1'$ is a hydrogen atom or $C_1$–$C_4$ alkyl, and
$R_2'$ is a hydrogen atom or an acetyl group.

4. The composition as claimed in claim 1 or 2, characterized in that the active constituent is 2-methylsulphinyl-3-nitrothiophene.

5. The composition as claimed in claim 1 or 2, characterized in that the active constituent is 2-methylsulphinyl-3-nitro-4-methylthiophene.

6. The composition as claimed in claim 1 or 2, characterized in that the active constituent is 2-ethylsulphinyl-3-nitrothiophene.

7. The composition as claimed in claim 1 or 2, characterized in that the active constituent is 2-methylsulphinyl-3-nitro-5-acetylthiophene.

8. The composition as claimed in claim 1 or 2, characterized in that the active constituent is 2-ethylsulphinyl-3-nitro-5-acetylthiophene.

9. A method of preventing or controlling fungus infections in agriculture and horticulture, comprising treating the crop to be protected or the infected crop with a composition of claim 1 in a dosage from 250 to 1,000 g of active substance per hectare.

10. A method of preventing infections by phytophagous microorganisms in agriculture and horticulture, comprising treating the soil destined for sowing or planting with a composition of claim 1 in a dosage from, 2 to 100 kg of active substance per hectare.

11. A method of preventing infections by phytophagous microorganisms in agriculture and horticulture, comprising treating the seed prior to sowing with a composition of claim 2, in a dosage from 100 to 1,500 mg of active substance per kg of seed.

* * * * *